United States Patent [19]

Ramachandran

[11] Patent Number: 5,640,219
[45] Date of Patent: Jun. 17, 1997

[54] APPARATUS FOR MEASURING PUPILLARY HEIGHT

[76] Inventor: Narayanan Ramachandran, 5G Fernwood Dr., Bolingbrook, Ill. 60440

[21] Appl. No.: 595,024

[22] Filed: Jan. 31, 1996

[51] Int. Cl.⁶ .......................................................... A61B 3/10
[52] U.S. Cl. ............................................... 351/204; 33/200
[58] Field of Search ................................ 351/200, 204, 351/158, 178, 246; 33/200

[56] References Cited

U.S. PATENT DOCUMENTS

| | | | |
|---|---|---|---|
| 2,491,312 | 12/1949 | Henry et al. | 33/200 |
| 3,981,081 | 9/1976 | Welch | 33/200 X |
| 3,987,554 | 10/1976 | Pastore | 33/200 |
| 4,055,900 | 11/1977 | Grolman et al. | 33/200 |
| 4,208,800 | 6/1980 | Grolman et al. | 33/200 |
| 4,653,192 | 3/1987 | Conrad et al. | 33/200 |
| 4,653,881 | 3/1987 | Joncour | 351/204 |
| 5,167,074 | 12/1992 | Weiss | 33/200 |
| 5,379,079 | 1/1995 | Kratky | 351/204 |

FOREIGN PATENT DOCUMENTS

| | | | |
|---|---|---|---|
| 1297357 | 6/1969 | Germany | 351/204 |

*Primary Examiner*—Huy Mai
*Attorney, Agent, or Firm*—Welsh & Katz, Ltd.

[57] ABSTRACT

An apparatus for measuring pupillary height of a pupil of a patient relative to a spectacle frame includes a housing having a distal end defining at least one target aperture. The housing has a proximal end opposite the distal end. A eye-piece is disposed toward the proximal end and permits an operator to observe the pupil of the patient through the target aperture such that the eye-piece, the target aperture, the spectacle frame, and the pupil of the patient are in operative alignment. Also included is a means for establishing and maintaining the housing at a fixed position relative to the spectacle frame, and an adjustable lower platform operatively coupled to the housing and vertically displaceble relative thereto. The lower platform is configured to engage a bottom edge of the spectacle frame. A measuring scale is operatively coupled to the lower platform such that vertical displacement of the lower platform causes corresponding vertical displacement of the measuring scale. The measuring scale is disposed in a fixed vertical relationship relative to the lower platform such that the measuring scale is displaced relative to the pupil of the patient when the lower platform is displaced to contact the bottom edge of the spectacle frame. A horizontal reference marker adjacent to the measuring scale is configured to be aligned with a center of the pupil and intersects the measuring scale. The operator aligning views the pupil of the patient through the eye-piece and aligns the horizontal reference marker with the center of the pupil such that the measurement of the pupillary height is determined by the intersection of the horizontal reference marker relative to the measuring scale.

19 Claims, 4 Drawing Sheets

APPARATUS FOR MEASURING PUPILLARY HEIGHT

BACKGROUND OF THE INVENTION

The present invention relates generally to an apparatus for measuring parameters required for mounting opthalamic lenses in a spectacle frame and more specifically to measuring pupillary height with respect to the bottom edge or lower eye wire of the spectacle frame.

In order to determine the pupillary height for placement of progressive addition lenses, a standard rule or scale has been typically used to estimate the height of the center of the pupil with respect to the lowest part of the lower eye wire of the spectacle frame so that the measurements can be conveyed to the lens maker. However, in such manual ruler techniques, inaccuracy can be easily introduced resulting in patient dissatisfaction.

An example of such a known ruler-type gauge is disclosed in U.S. Pat. No. 3,987,554 issued on Oct. 26, 1976 to J. Pastore. The known gauge is inserted into the bevel (lens well) of the lower eye wire of the spectacle frame at its lowest part and by reading the graduation where an imaginary horizontal line passing through the center of the pupil would intersect the gauge, the pupillary height is estimated. However, the device is inconvenient to use and is prone to measurement errors caused by the following factors: 1) the patient's eyes would wander; 2) the optician approximates the center of the corneas or pupil by observation; 3) the optician approximates the imaginary line; 4) the optician approximates the lowest portion of the lower eye wire; and 5) proximity between patient and optician could cause eye strain to both the patient and the optician.

Other devices exist which include an ocular or eye-piece through which the optician observes the eye of the patient. The eye-piece typically includes a cross-hair or horizontal line which is aligned with the center of the eye. An example of such a known ocular positioning apparatus is disclosed in U.S. Pat. No. 5,167,074 issued on Dec. 1, 1992 to M. Weiss. The device provides a chin rest for maintaining the stability of the patient's head. The optician observes the center of the eye or other reference points on the patient's face through an ocular and moves the ocular along a vertical axis until the cross-hairs of the ocular are aligned with the appropriate reference point. The vertical distance traveled by the ocular represents the pupillary height of the patient. However, such a known device is extremely cumbersome and requires placement on a suitable table top and is preferably, permanently mounted to the table top. A significant drawback of this known device is that the cross-hairs of the optician's eye-piece are disposed relatively far away from the patient's eye. When the optician attempts to align the cross-hairs with the eye, the measurement of the distance, or the vertical distance that the eye-piece is displaced, depends upon the angle through which the optician views the patient's eye each time. This may result in a significant parallax error. During each attempt to align the cross-hairs with the eye, the optician must look through the exact center of the eye-piece to avoid introduction of such parallax errors. Such a task is difficult to accurately perform and often results in measurement errors.

Accordingly, it is an object of the present invention to substantially overcome the above-described problems.

It is another object of the present invention to provide a pupillary height meter which substantially eliminates parallax error.

It is a further object of the present invention to provide a pupillary height meter which measures the vertical distance from the bottom of the spectacle frame to the center of the cornea.

It is also an object of the present invention to provide a pupillary height meter which independently measures the pupillary height of each eye.

It is still an object of the present invention to provide a pupillary height meter that is physically compact and is easy to operate.

SUMMARY OF THE INVENTION

The disadvantages of present pupillary height meters are substantially overcome with the present invention by providing a novel pupillary height meter that accurately determines the height of the pupil measured between the bottom of the spectacle frame and the center of the cornea, substantially free of parallax error. The apparatus is physically compact and is quickly and easily secured to the forehead of the patient. The apparatus is compact and need not envelope the entire spectacle frame and may be smaller in height than the height of the spectacle frame. Placement of the apparatus relative to the patient's head is independent of pupil height since all measurements are performed relative to the bottom of the spectacle frame.

The optician need only attach a flexible band around the patient's forehead and adjust an upper platform to contact the top edge of the spectacle frame. This prevents movement of the spectacle frame on the patient's head. The optician then adjusts a pair of lower platforms so that each lower platform contacts the bottom edge of the spectacle frame. Once the lower platforms are adjusted, the optician observes the patient's eyes through the eye-piece and aligns the horizontal cross-hair with the corneal reflection. The intersection of the horizontal cross-hair relative to a transparent scale or vernier, as seen through the eye-piece, directly corresponds to the measurement of pupillary height. Since the horizontal cross-hair is adjacent the scale, and also due to the fact that the corneal reflection, the scale, and the horizontal cross-hair are all at the same height as the optician looks through the ocular, virtually no parallax error results.

More specifically, the pupillary height measuring apparatus of the present invention measures the pupillary height of a pupil of a patient relative to a spectacle frame that the patient has selected. The apparatus includes a housing having a distal end defining at least one target aperture. The housing has a proximal end opposite the distal end. An eye-piece is disposed at the proximal end and permits an operator to observe the pupil of the patient through the target aperture such that the eye-piece, the target aperture, the spectacle frame, and the pupil of the patient are in operative alignment.

Also included is a means for establishing and maintaining the housing at a fixed position relative to the spectacle frame, and an adjustable lower platform operatively coupled to the housing and vertically displaceble relative thereto. The lower platform is configured to tangentially engage the bottom edge or eyewire of the spectacle frame. A measuring scale is operatively coupled to the lower platform such that vertical displacement of the lower platform causes corresponding vertical displacement of the measuring scale. The measuring scale is disposed in a fixed vertical relationship relative to the lower platform such that the measuring scale is displaced relative to the pupil of the patient when the lower platform is displaced to contact the bottom edge of the spectacle frame.

A horizontal reference marker adjacent the measuring scale is configured to be aligned with the center of the pupil and intersects the measuring scale. The operator aligning views the pupil of the patient through the eye-piece and aligns the horizontal reference marker with the center of the pupil such that the measurement of the pupillary height is determined by the intersection of the horizontal reference marker relative to the measuring scale.

BRIEF DESCRIPTION OF THE DRAWINGS

The features of the present invention which are believed to be novel are set forth with particularity in the appended claims. The invention, together with further objects and advantages thereof, may best be understood by reference to the following description in conjunction with the accompanying drawings.

DETAILED DESCRIPTION OF THE INVENTION

Figure 1:
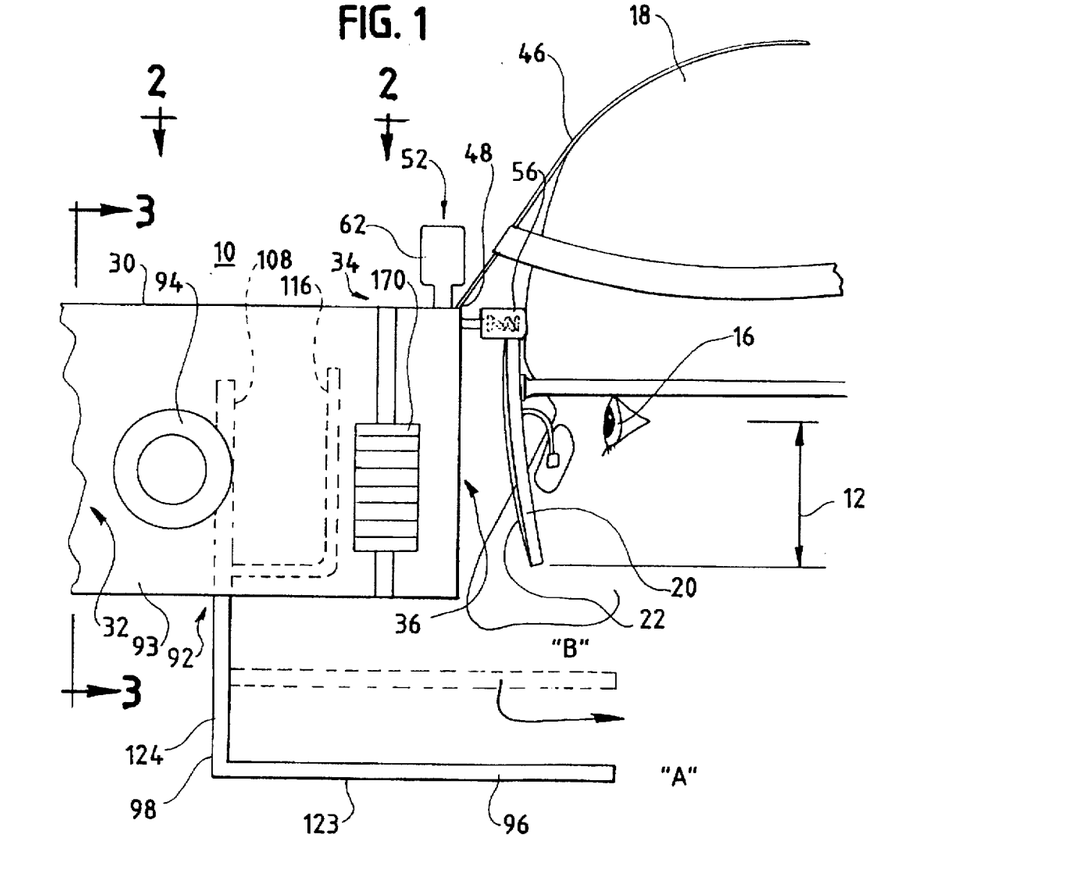
FIG. 1 is a side elevational view of a specific embodiment of a pupillary height measuring apparatus, according to the present invention.
Figure 2:
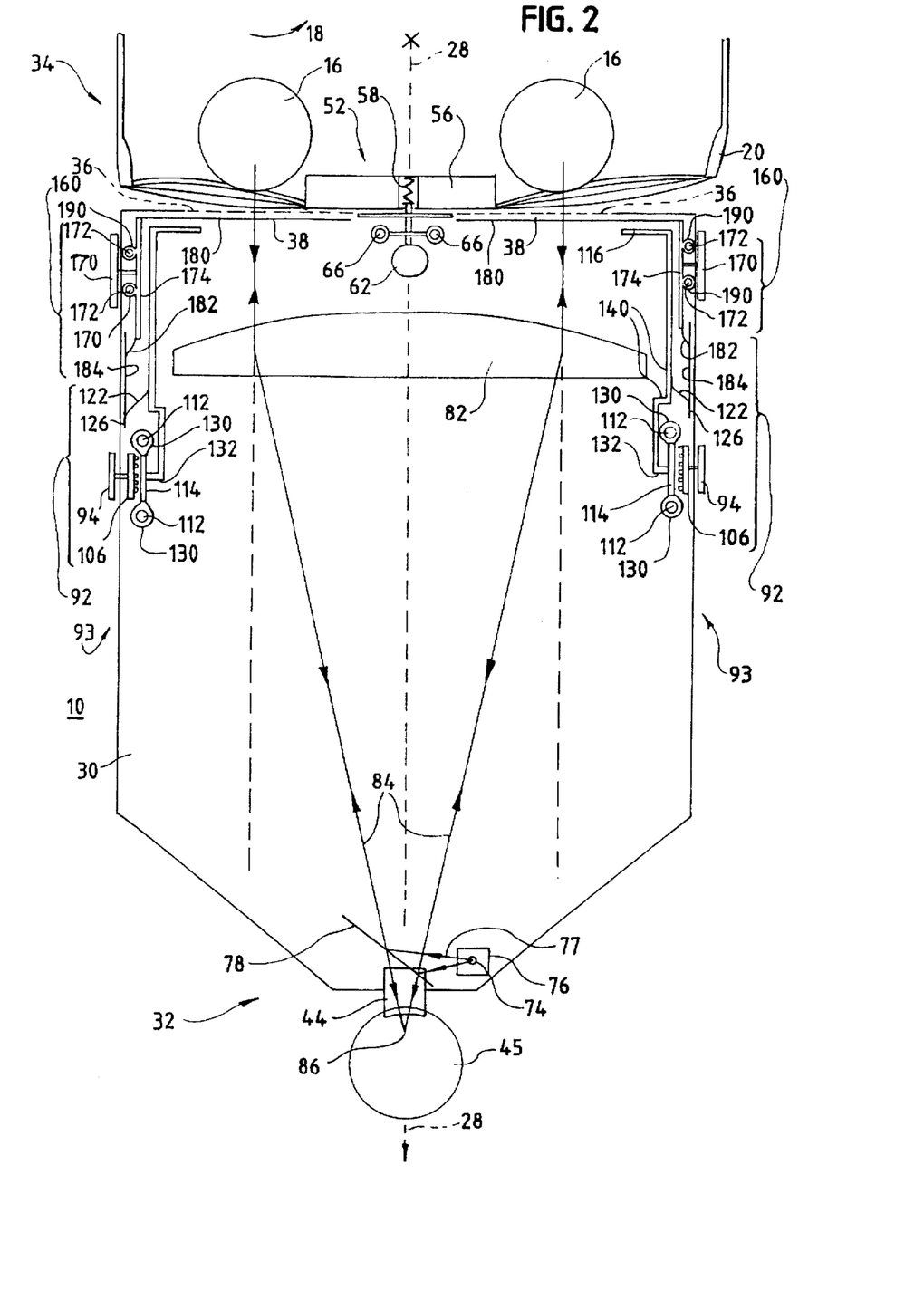
FIG. 2 is a top plan sectional view of the pupillary height measuring apparatus shown in FIG. 1 taken along the line 2—2 of FIG. 1 in the direction generally indicated.
Figure 3:
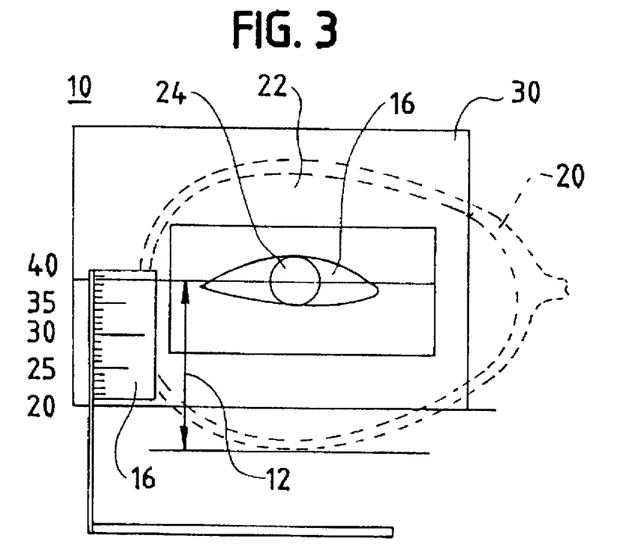
FIG. 3 is a front sectional view of the pupillary height measuring apparatus shown in FIG. 1 taken along the line 3—3 of FIG. 1 in the direction generally indicated particularly showing the measured parameters of the eye.

Referring now to FIGS. 1–3, an apparatus 10 for measuring pupillary height is shown generally in FIGS. 1 and 2. FIGS. 1 and 2 illustrate the apparatus 10 while FIG. 3 illustrates the particular parameter measured. The apparatus 10 measures pupillary height 12 (FIG. 3) of each eye 16 of a patient 18 relative to a spectacle frame 20 where the frame contains a pair of lenses 22. It is extremely important to measure the exact pupillary height 12 when mounting progressive lenses in the frame 20. The pupillary height 12 is the distance between the center of the patient's pupil 24 (as determined by the corneal reflection, described in greater detail hereinafter) and the lowest portion of the lower eye wire of the spectacle frame 20.

Note that all lateral components shown in FIG. 2 are symmetric about a longitudinal axis 28 and that the left half of the apparatus 10 is identical to the right half of the apparatus. Accordingly, identical reference numerals identify like structures. A housing 30 is provided which may be constructed from plastic or metal or any other suitable material. As best seen in FIG. 2, the housing 30 is generally rectangular or box-like in shape and may taper toward a proximal end 32. A distal end 34 disposed opposite the proximal end 32 is relatively flat and defines two target apertures 36 each having a protective transparent glass or plastic covering 38 (FIG. 2) through which the patient's 18 line of sight is directed. The eyes 16 of the patient 18 are directed such that they are in operative alignment with an eye-piece or ocular 44 disposed at the proximal end 32. An optician or technician 45 observes the patient's eyes 16 through the eye-piece 44 and through the target apertures 36 and performs the required measurements, as will be described in greater detail below.

A flexible band 46 (FIG. 1) is configured to wrap around the forehead of the patient 18 to fixedly secure and maintain the housing 30 relative to the patient. The band 46 may be formed from soft plastic or fabric and may be stretchable to conform to different head sizes, including adults and children. Alternately, the band 46 may be adjustable having belt-like adjustments or may include hook and loop-type fasteners, as is known in the art. The band 46 is pivotally mounted to the distal end 34 of the housing and is configured to pivot vertically relative to the patient 18. The apparatus 10 should be centered on the forehead of the patient 18 so as to retain the longitudinal axis 28 (FIG. 2) in a centered orientation with respect to the patient's eyes 16. Accordingly, as the housing 30 is upwardly pivoted with respect to the band 46, the distal end 34 moves away from the patient's face. Conversely, as the housing 30 is downwardly pivoted with respect to the band 46, the distal end 34 moves closer to the patient's face. A hinge 48 couples the band 46 to the housing 30 to achieve the above-described relationship between the band and the housing. The hinge 48 inhibits lateral movement of the patient 18 with respect to the housing 30 so that the patient is always centered with respect to longitudinal axis 28 (FIG. 2).

Alternately, the band 46 may be replaced with a soft cushioning footer or rubber bumper (not shown) attached to the housing 30. The footer is gently pressed against the patient's 18 forehead since the apparatus 10 is relatively light in weight permitting the optician 45 to hold the apparatus 10 in place while performing the measurement. The optician 45 needs to hold the apparatus 10 in a steady manner while performing the task.

Figure 4:
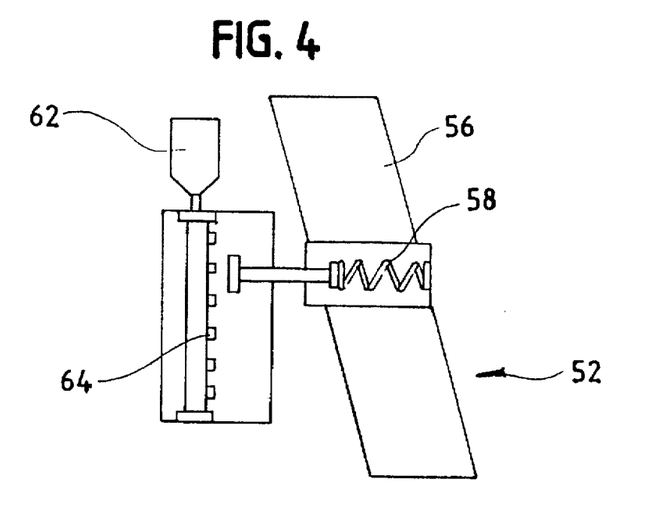
FIG. 4 is an enlarged side view of an upper guide shown in FIG. 2.

Referring now to FIGS. 2 and 4, FIG. 4 illustrates an upper guide mechanism 52 connected to the housing 30. The upper guide mechanism 52 is configured to extend away from the housing 30 to engage a top edge of the spectacle frame 20 to establish and maintain the housing at a fixed vertical height relative to the spectacle frame. The upper guide mechanism 52 includes a planar shelf 56 which extends away from the housing 30. The shelf 56 extends outwardly and is adjusted vertically until it contacts the top edge of the spectacle frame 20. The shelf 56 is biased outwardly toward the patient 18 with a spring 58 so that the shell contacts the forehead of the patient while simultaneously contacting the top edge of the spectacle frame 20.

The planar shelf 56 is adjusted in the vertical direction by turning an upper guide adjustment knob 62. The knob 62 is connected to a threaded bolt or worm gear 64 (FIG. 4) which is secured within the housing by a sleeve and upright arrangement 66 (FIG. 2), as is known in the art. When the knob 62 is rotated in the clockwise direction, the planar shelf 56 moves upwardly. Similarly, when the knob 62 is rotated in the counter-clockwise direction, the planar shelf 56 moves downwardly. Thus, the upper guide mechanism 52 establishes the housing 30 at fixed vertical height relative to the spectacle frame 20 so that repeatable measurements may be taken. However, any suitable means for fixing the vertical height between the housing 30 and the spectacle frame 20 may be used. Note, that the relative position between the housing 30 and the spectacle frame 20 does not affect the measurement of pupillary height 12 (FIG. 3), as will be described in greater detail hereinafter. The upper guide 56 is configured to prevent the spectacle frame 20 from moving upwards relative to the patient's 18 habitual wearing position when the lower platforms 96 engage the lower eyewires of the frame 20.

Referring now to FIG. 2, the optics of the apparatus 10 are shown generally. A light source 74 is disposed in a shielded housing 76 and directs a beam of light 77 toward a planar mirror 78 disposed at a forty-five degree angle to the incident light beam. The planar mirror 78 reflects the light toward a convex lens 82 along a light path indicated by reference numeral 84. The convex lens 82 is disposed toward the distal end 34 of the housing 30 and refracts the light beam 84 into the patient's eyes 16 in a parallel configuration. The light is then reflected off of the cornea of the eyes 16 and is retraced through the convex lens 82 toward the optician 45. A portion of the reflected light passes just below the planar mirror 78 and enters the ocular 44 and is viewed by the optician 45. In this way, the optician 45 can see the image of the light source 74 as the corneal reflection of the patient's eyes 16. This establishes the exact center of the pupil of the eye 16. The planar mirror 78 may also be partially transmissive so that the optician 45 can view a portion of the light reflected back from the patient 18 as it passes through the mirror 78.

The convex lens 82 is selected so that its focal length allows the light from the light source 74 to be rendered in a parallel orientation toward the patient's eyes 16. Further, the focal length of the lens 82 is the same distance as the distance between the light source 74 and the lens. This distance is also equal to the distance between the lens and the point 86 where the light converges inside the optician's 45 eye.

Figure 5:
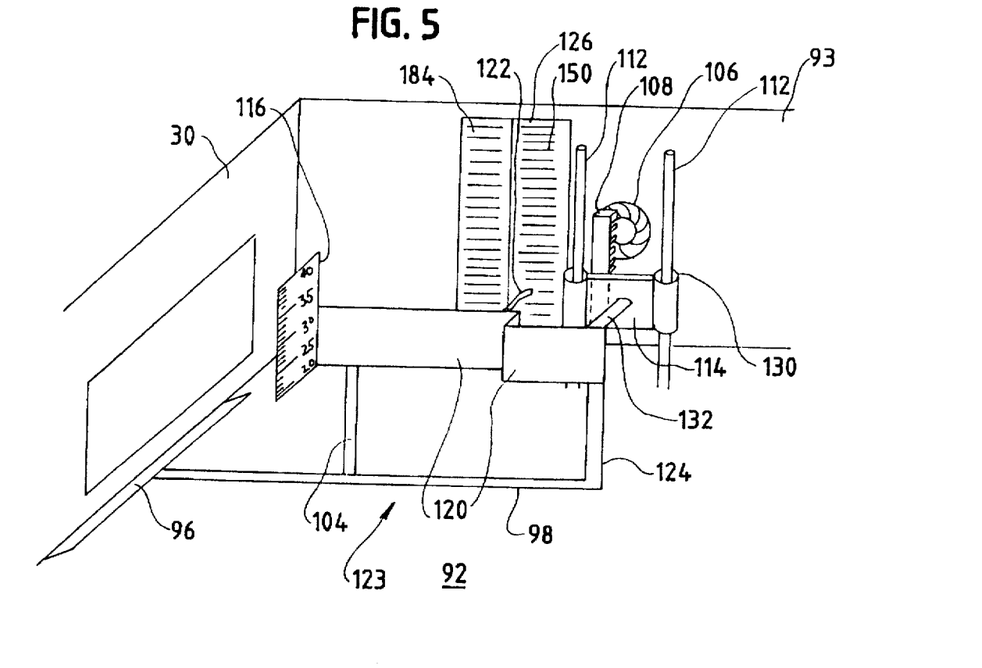
FIG. 5 is an enlarged perspective view of a lower platform mechanism shown in FIG. 2.
Figure 6:
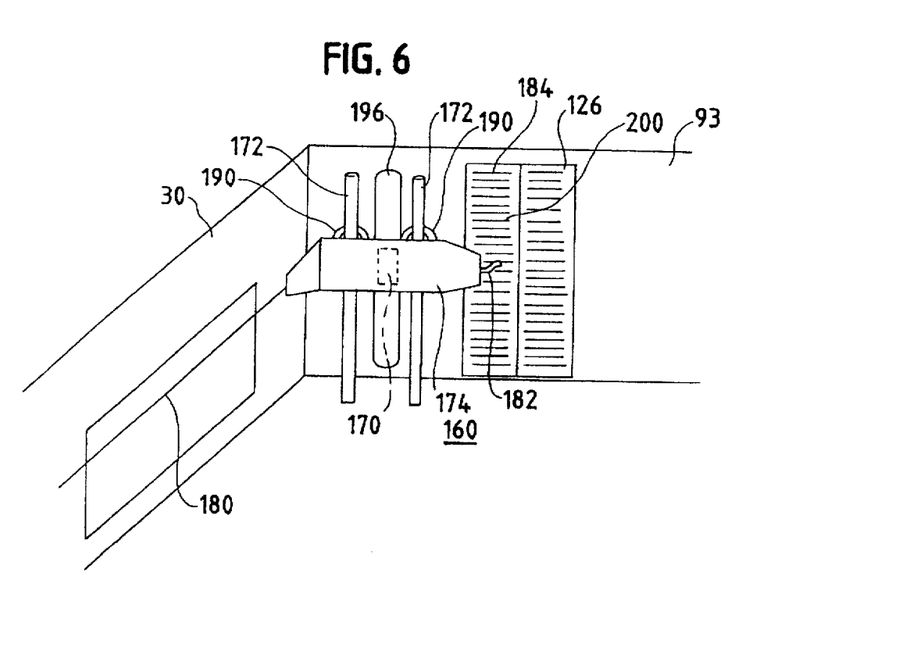
FIG. 6 is an enlarged perspective view of a horizontal reference marker mechanism shown in FIG. 2.

Referring now to FIGS. 1, 2 and 5, FIG. 2 shows the housing 30 and a top view of a lower platform mechanism 92 generally, while FIG. 5 illustrates an enlarged detailed illustration of the right side lower platform mechanism shown from within the housing. Note that two lower platform mechanisms 92 exist, each disposed on opposite lateral sides of the housing 30 and directed toward measuring the pupillary height 12 of the left and right eye, respectively. Each lower platform mechanism 92 is independently adjustable relative to the other to facilitate measurement of the pupillary height 12 of each eye 16 independently.

The lower platform mechanism 92 includes an adjustment knob 94 (FIGS. 1–2), a lower platform 96 (FIG. 1 and 5), a lower platform support arm 98 (FIGS. 1 and 5), a lower platform brace 104, a crown wheel 106, a toothed rod 108, guide rails 112, a lower platform slider body 114, a measuring scale 116, a scale support arm 120, an electrical wiper 122, and a printed circuit board 126. The function of the lower platform mechanism 92 is to move the lower platform 96 in a vertical direction until the lower platform engages the bottom rim of the patient's spectacle frame 20. Accordingly, the lower platform 96 is external to the housing 30 and is supported by the lower platform support arm 98 which extends outside of the housing 30 but enters the housing 30 through an aperture (not shown) in the bottom of the housing. The lower platform brace 104 (FIG. 5) may be included to prevent the lower platform support arm 98 from flexing such that the lower platform 96 is maintained in a parallel orientation relative to the bottom of the housing 30.

The lower platform support arm 98 is formed from a horizontal portion 123 and a vertical portion 124 connected to the horizontal portion at substantially ninety degrees. The horizontal portion 123 is substantially disposed external to the housing 30 and extends away from the housing 30 to permit the lower platform 96 to be displaced vertically until it contacts the lower edge of the spectacle frame 20. The vertical portion 124, including the lower platform brace 104 (not shown in FIG. 1) is partially received within the housing 30 and enters the housing through an aperture or slot (not shown).

The slider body 114 has two cylindrical throughbores 130 or tube-like structures affixed thereto through which the fixedly mounted guide rails 112 are received. The guide rails 112 are mounted to the side or to the bottom of the housing 30 so that the slider body 114 slides vertically along the guide rails 112. Since the lower platform support arm 98 is rigidly affixed to the slider body 114, the lower platform support arm and the lower platform 96 move in unison with the slider body.

Note that the lower platform support arm 98 is attached to the slider body through a bridge member 132. The bridge member 132 provides a rigid mechanical link so that the lower platform 96 and corresponding scale support arm 120 can move in an unobstructed manner. The scale support arm 120 is also rigidly attached to the bridge member 132 and supports the scale 116 in a fixed relationship relative to the slider body 114. Thus, when the slider body 114 is vertically displaced, the lower platform 96 and the measuring scale 116 move simultaneously and always maintain their relative positions. Since the measuring scale 116 is operatively connected to the lower platform 96, vertical displacement of the lower platform causes corresponding vertical displacement of the scale such that the scale always measures the pupillary height 12 of the eye 16 relative to the bottom edge of the spectacle frame 20 when the lower platform 96 engages the bottom edge of the spectacle frame.

The measuring scale 116 may be a transparent ruler-like vernier with millimeter markings or gradations engraved or printed on its surface. The measuring scale 116 is disposed toward the distal end 34 of the housing 30 so that it is proximal the target aperture 36 and the eye 16 of the patient 18. Note that the measuring scale 116 is essentially a vertical extension of the lower platform 96. The millimeter engravings on the measuring scale 116 begin at twenty millimeters since the lowest end of the measuring scale disposed within the housing is always twenty millimeters in height above the lower platform 96. In this way, once the lower platform 96 is positioned against the lower edge of the spectacle frame 20, the measuring scale 116 will always indicate the pupillary height 12 relative to the lower edge of the spectacle frame.

Proximity of the scale 116 toward the eye 15 of the patient 18 substantially reduces or eliminates parallax error since the optician 45 views the center of the eye 18 through the eye-piece 44 located at the other end (proximal end 32) of the housing 30. Thus, when the pupillary height 12 is measured against the measuring scale 116, as will be described in greater detail hereinafter, almost no viewing angle error exists since the scale 116 is disposed proximal to the eye 16.

The slider body 114 is fixedly attached to the toothed rod 108 which operatively engages the crown wheel 106 (FIG. 5). The toothed rod 108 and crown wheel 106 function like a worm gear and crank so that when the crown wheel is rotated, the toothed rod and hence, the slider body 114, are correspondingly vertically displaced. The adjustment knob 94 (FIG. 1) is directly connected to the crown wheel 106 external to the housing 30 so that the optician 45 can perform the adjustment. The adjustment knob 94 is disposed on the external surface of the housing 30 and permits the optician 45 to conveniently and precisely control the vertical position of the lower platform 96. Note that there are two adjustment knobs 94 disposed on opposite sides of the housing 30 to permit independent control of the left and right side lower platforms 96.

The electrical wiper 122 or electrical contact (FIG. 5) is fixed to the scale support arm 120 and is configured to engage exposed electrical contacts 150 on the printed circuit board 126 which is mounted against the side of the housing 30. When the lower platform 96 and the measuring scale 116 are vertically displaced, the wiper 122 makes electrical contact at varying positions along the printed circuit board 126. The printed circuit board 126 may contain resistive elements or may contain a series of contact points such that contact therewith can be sensed by a microprocessor or discrete logic components, as is known in the art. Thus, information corresponding to the vertical position of the measuring scale 116 is available to electrical components so that a digital readout of the pupillary height 12 can be displayed in addition to visual observation of the measuring scale, as will be described below. Note, to obtain pupillary height based upon the wiper 122 position, additional information, such as the point where the center of the pupil intersects the measuring scale 116, is required, as will be described hereinafter. A display device (not shown) provides a digital readout or other visual indication of the pupillary height 12 and may be incorporated into the housing 30. Alternately, the display may be external to the housing.

Referring now to FIGS. 1, 2, 5, and 6, FIG. 6 is an enlarged detailed illustration of a horizontal reference marker mechanism 160 shown from within the housing 30. Note that two horizontal reference marker mechanisms 160 exist, each disposed on opposite lateral sides of the housing 30 and directed to measuring the pupillary height 12 of the left and right eyes 16, respectively. Each horizontal reference marker mechanism 160 is independently adjustable relative to the other to facilitate measurement of the pupillary height 12 of each eye 16 independently. Also note that with respect to FIGS. 5 and 6, that both the lower platform mechanism 92 and the horizontal reference marker mechanism 160 exist adjacent to each other on each side of the housing, as shown in FIG. 2, but are shown separated for purposes of illustration only in FIGS. 5 and 6, respectively. Thus, the left side of the housing 30 includes a lower platform mechanism 92 and a horizontal reference marker mechanism 160 while the right side of the housing includes identical elements.

The horizontal reference marker mechanism 160 includes an adjustment knob 170 (FIGS. 1 and 6) or slider knob, guide rails 172, a slider body 174, a marker needle 180, an electrical wiper 182, and a printed circuit board 184. The function of the horizontal reference marker mechanism 160 is to vertically displace the marker needle 180 until it is in alignment with the center of the pupil of the eye 16. The marker needle 180 is adjacent the measuring scale 116 such that the intersection thereof can be observed by the optician 45. The position on the measuring scale 116 intersected by the marker needle 180 represents the measurement of pupillary height 12.

The marker needle 180 is a rigid metal needle or other thin marking structure rigidly affixed to the slider body 174 at substantially ninety degrees. The marker needle 180 always remains parallel to the bottom of the housing 30 as the slider body 174 is vertically displaced. The slider body 174 has two cylindrical throughbores 190 or tube-like structures affixed thereto through which the fixedly mounted guide rails 172 are received. The guide rails 172 are mounted to the side or to the bottom of the housing 30 and are similar to the guide rail and slider of the lower platform mechanism 92. The slider body 174 is configured to slide vertically along the guide rails 172. Since the marker needle 180 is rigidly affixed to the slider body 174, it moves in unison therewith.

The adjustment knob 170 is disposed on the outside of the housing 30 and is connected to the slider body 174 through a slot 196 (FIG. 6) disposed in the side of the housing. The adjustment knob 170 is essentially a slide knob which the user displaces vertically to displace the marker needle 180.

The marker needle 180 is adjacent to the measuring scale 116 and is disposed just behind the scale 116 where the scale is preferably transparent. Since both the measuring scale 116 and the marker needle 180 are adjacent to each other and are both disposed toward the eye 16 of the patient 18, parallax error is substantially reduced or eliminated. Virtually no angular error is induced when the marker needle 180 is aligned with the corneal reflection of the eye 16.

The electrical wiper 182 is fixed to the slider body 174 and engages exposed electrical contacts 200 on the printed circuit board 184 which is mounted to the side of the housing 30. When the slider body 174 is displaced, the wiper 182 makes electrical contact at varying positions along the printed circuit board 184. The printed circuit board 184 may contain resistive elements or may contain a series of contact points such that contact therewith may be sensed by a microprocessor or by discrete logic components, as is known in the art. Thus, information corresponding to the vertical position of the slider body and hence, the marker needle 180 is available to the electrical components or processor.

With the position of both electrical wipers 182 and 122 known to the electronics of the apparatus 10, a difference in position can easily be determined, as is known in the art. The difference in wiper 122 and 182 positions represents the difference in position between the marker needle 180 and the absolute position of the scale 116. This distance represents the pupillary height 12 and may be displayed in digital format or may be determined by visual observation. Digital display of the pupillary height 12 may be performed in addition to or to the exclusion of visual observation of the measuring scale 116.

Referring now to FIGS. 1–3, in operation, the housing 30 is secured to the patient 18 such that the patient is directed to look into the target apertures 36 of the housing. Note that the pupillary height 12 for each eye is measured independently using the below-described method. The flexible band 46 is fitted and secured about the forehead of the patient 18 and the optician 45 adjusts the upper guide adjustment knob 62 until the planar shelf 56 engages the upper edge of the patient's spectacle frame 20. This prevents the spectacle frame 20 from inadvertently becoming displaced relative to the housing 30. Next, the optician 45 turns on the apparatus to illuminate the internal lamp 74 and directs the patient 18 to focus on the light source. The optician 45 then looks into the eye-piece 44 and observes the patient's eyes 18.

Next, the optician 45 turns the lower platform adjustment knob 94 to displace the lower platform 96 from the position shown by reference letter "A" (FIG. 1) to the position shown by reference letter "B". This causes the lower platform 96 to engage the lower edge of the spectacle frame 20 so that the spectacle frame is bounded between the upper guide 56 and the lower platform. The optician 45 then aligningly views the corneal refection of the patient's eye through the eye-piece 44 and slides the reference marker adjustment knob 170 until the marker needle 180 is in the exact center of the corneal reflection.

The optician 45 then reads the point on the measuring scale 116 where the marker needle 180 crosses the measuring scale and makes note of the measurement. This measurement represents the pupillary height 12 as measured from the bottom of the spectacle frame 20 to the center of the patient's pupil, as indicated by the corneal reflection. This procedure is performed for the left eye and the right eye.

Note that the spectacle frames 20 may have a particular thickness if they fully enclose the lenses 22 or may have no thickness at the bottom of the lenses if the frame is affixed to the lenses only at the top portion of the lenses (rimless frames). An offset switch (not shown) may be connected to the printed circuit boards 126 and 184 which corresponds to the type of spectacle frames worn by the patient 18. Most plastic frames have a thickness of about 2.0 millimeters and an inside bevel of about 0.5 millimeter while metal frames have a total thickness of about 1.0 millimeters and an inside bevel of about 0.5 millimeters. Depending upon the selection of the offset switch, the estimated thickness of the frames 20 may be automatically subtracted from the pupillary height 12 measurement to yield a more accurate reading. Obviously, if the optician is reading the measurement from the measuring scale 116 without benefit of a digital display, the optician 45 can easily perform the subtraction mentally.

Specific embodiments of an apparatus for measuring pupillary height according to the present invention have been described for the purpose of illustrating the manner in which the invention may be made and used. It should be understood that implementation of other variations and modifications of the invention and its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

What is claimed is:

1. An apparatus for measuring pupillary height of a pupil of a patient relative to a spectacle frame, the apparatus comprising:

a housing having a distal end defining at least one target aperture;

said housing having a proximal end opposite the distal end;

an eye-piece disposed toward the proximal end, said eye-piece permitting an operator to observe the pupil of the patient through the target aperture such that the eye-piece, the target aperture, the spectacle frame, and the pupil of the patient are in operative alignment;

means for establishing and maintaining the housing at a fixed position relative to the spectacle frame;

an adjustable lower platform external to the housing and operatively coupled thereto, said lower platform vertically displacable relative to the housing and configured to engage a bottom edge of the spectacle frame during vertical displacement of the lower platform;

a measuring scale operatively coupled to the lower platform such that vertical displacement of the lower platform causes corresponding vertical displacement of the measuring scale, said measuring scale disposed in a fixed vertical relationship relative to the lower platform such that the measuring scale is displaced relative to the pupil of the patient when the lower platform is displaced to contact the bottom edge of the spectacle frame;

a horizontal reference marker adjacent the measuring scale configured to be aligned with a center of the pupil, said horizontal reference marker intersecting the measuring scale; and said operator aligning viewing the pupil of the patient through the eye-piece and aligning the horizontal reference marker with the center of the pupil such that the measurement of the pupillary height is determined by the intersection of the horizontal reference marker relative to the measuring scale.

2. The apparatus according to claim 1 wherein the lower platform includes a vertical portion operatively coupled to the measuring scale, and a horizontal portion connected to the vertical portion at substantially a ninety degree angle, said vertical portion partially received within the housing, said horizontal portion extending away from the housing and configured to engage the bottom edge of the spectacle frame.

3. The apparatus according to claim 1 further including two lower platforms, each said lower platform operatively coupled to a measuring scale, each lower platform being independently adjustable relative to the other lower platform to facilitate measurement of the pupillary height of each eye of the patient.

4. The apparatus according to claim 1 wherein the measuring scale and the horizontal reference marker are disposed toward the target apertures and away from the eye-piece to substantially eliminate a parallax measurement error.

5. The apparatus according to claim 1 wherein the measuring scale and the horizontal reference marker are adjacent each other to substantially eliminate a parallax measurement error.

6. The apparatus according to claim 1 wherein the center of the pupil is determined by a corneal reflection of the pupil viewed by the operator through the eye-piece.

7. The apparatus according to claim 1 wherein a lower platform control mechanism operatively coupled to the housing controls the vertical position of the lower platform.

8. The apparatus according to claim 1 wherein a reference marker control mechanism operatively coupled to the housing controls the position of the horizontal reference marker.

9. The apparatus according to claim 1 wherein a lower platform control mechanism operatively coupled to the housing controls the vertical position of the lower platform, and a reference marker control mechanism operatively coupled to the housing controls the position of the horizontal reference marker.

10. The apparatus according to claim 9 wherein the lower platform control mechanism and the reference marker control mechanism are operatively coupled to a circuit which provides an electrical signal corresponding to the measurement of the difference in vertical distance of the horizontal reference marker relative to the measuring scale.

11. The apparatus according to claim 10 further including a display device responsive to the electrical signal to provide a visual indication of the pupillary height.

12. The apparatus according to claim 1 further including a band configured to wrap around a portion of a head of the patient to fixedly secure the housing relative to the patient, said band pivotally attached to the distal end of the housing.

13. An apparatus for measuring pupillary height of a pupil of a patient relative to a spectacle frame, the apparatus comprising:

a housing having a distal end defining at least one target aperture;

said housing having a proximal end opposite the distal end;

an eye-piece disposed toward the proximal end, said eye-piece permitting an operator to observe the pupil of the patient through the target aperture such that the eye-piece, the target aperture, the spectacle frame, and the pupil of the patient are in operative alignment;

an upper guide connected to the housing configured to extend away from the housing to engage a top edge of the spectacle frame to establish and maintain the housing at a fixed position relative to the spectacle frame;

an adjustable lower platform external to the housing and operatively coupled thereto, said lower platform vertically displacable relative to the housing and configured to engage a bottom edge of the spectacle frame during vertical displacement of the lower platform;

a measuring scale operatively coupled to the lower platform such that vertical displacement of the lower platform causes corresponding vertical displacement of the measuring scale, said measuring scale disposed in a fixed vertical relationship relative to the lower platform such that the measuring scale is displaced relative to the pupil of the patient when the lower platform is displaced to contact the bottom edge of the spectacle frame;

a horizontal reference marker disposed adjacent the measuring scale configured to be aligned with a center of the pupil, said horizontal reference marker intersecting the measuring scale; and said operator aligning viewing the pupil of the patient through the eye-piece and aligning the horizontal reference marker with the center of the pupil such that the measurement of the pupillary height is determined by the intersection of the horizontal reference marker relative to the measuring scale.

14. The apparatus according to claim 13 wherein the upper guide is coupled to a biasing mechanism configured to urge the upper platform toward the spectacle frame of the patient so that the spectacle frame is bounded between the upper guide and the lower platform.

15. The apparatus according to claim 13 wherein the lower platform includes a vertical portion operatively coupled to the measuring scale, and a horizontal portion connected to the vertical portion at substantially a ninety degree angle, said vertical portion partially received within the housing, said horizontal portion extending away from the housing and configured to engage the bottom edge of the spectacle frame.

16. The apparatus according to claim 13 further including two lower platforms, each said lower platform operatively coupled to a measuring scale, each lower platform being independently adjustable relative to the other lower platform to facilitate measurement of the pupillary height of each eye of the patient.

17. The apparatus according to claim 13 wherein the measuring scale and the horizontal reference marker are disposed toward the target apertures and away from the eye-piece to substantially eliminate a parallax measurement error.

18. The apparatus according to claim 13 wherein the measuring scale and the horizontal reference marker are adjacent to each other to substantially eliminate a parallax measurement error.

19. A method for measuring pupillary height of a pupil of a patient relative to a spectacle frame, the method comprising the steps of:

operatively placing a housing having a proximal and distal end about the head of the patient, said distal end defining at least one target aperture so that a line of sight of the patient is directed into the target apertures;

establishing and maintaining the housing at a fixed position relative to the spectacle frame;

observing the pupil of the patient by viewing the pupil through an eye-piece disposed toward the proximal end of the housing such that the eye-piece, the target aperture, the spectacle frame, and said pupil of the patient are in operative alignment;

vertically adjusting a lower platform to engage a bottom edge of the spectacle frame, said lower platform external to the housing and operatively coupled thereto, said lower platform vertically displacable relative to the housing and configured to engage the bottom edge of the spectacle frame during vertical displacement of the lower platform;

aligning a horizontal reference marker with a center of the pupil; and observing the intersection of the horizontal reference marker with a measuring scale, said measuring scale operatively coupled to the lower platform such that vertical displacement of the lower platform causes corresponding vertical displacement of the measuring scale, said intersection of the horizontal reference marker with the measuring scale representing the pupillary height of the patient.

* * * * *